United States Patent
Alabbad

(10) Patent No.: US 12,222,273 B2
(45) Date of Patent: Feb. 11, 2025

(54) APPARATUS FOR REAL-TIME MONITORING OF ORGANIC MATTER POROSITY EVOLUTION USING SELECTIVE PHOTO-THERMAL LASER AS A HEAT SOURCE TO TARGET ORGANIC MATTER ONLY

(71) Applicant: SAUDI ARABIAN OIL COMPANY, Dhahran (SA)

(72) Inventor: Abrar Alabbad, Al-Jish (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 352 days.

(21) Appl. No.: 17/746,478

(22) Filed: May 17, 2022

(65) Prior Publication Data
US 2023/0375457 A1    Nov. 23, 2023

(51) Int. Cl.
*G01N 15/08*    (2006.01)
*G01N 23/046*    (2018.01)
*G01N 23/083*    (2018.01)
*G01N 33/24*    (2006.01)

(52) U.S. Cl.
CPC ....... *G01N 15/0806* (2013.01); *G01N 23/046* (2013.01); *G01N 23/083* (2013.01); *G01N 33/24* (2013.01); *G01N 2223/3106* (2013.01); *G01N 2223/616* (2013.01)

(58) Field of Classification Search
CPC ......... G01N 15/0806; G01N 2223/616; G01N 2223/3106; G01N 23/046; G01N 23/083
See application file for complete search history.

(56) References Cited

U.S. PATENT DOCUMENTS

| | | | | |
|---|---|---|---|---|
| 5,933,473 A | * | 8/1999 | Kitaguchi | G01N 23/046 378/57 |
| 8,080,796 B1 | * | 12/2011 | Van Neste | G01N 21/3563 250/338.1 |
| 9,128,210 B2 | * | 9/2015 | Pomerantz | G01N 33/241 |
| 10,139,355 B1 | * | 11/2018 | Li | G01N 23/046 |

(Continued)

FOREIGN PATENT DOCUMENTS

| CN | 103278428 B | 5/2015 |
|---|---|---|
| CN | 106644659 A | 5/2017 |

(Continued)

OTHER PUBLICATIONS

Volkov, Dmitry S., et al. "Photoacoustic and photothermal methods in spectroscopy and characterization of soils and soil organic matter", Photoacoustics. Mar. 2020, pp. 1-18, [18 Pages].

(Continued)

*Primary Examiner* — Dani Fox
*Assistant Examiner* — Soorena Kefayati
(74) *Attorney, Agent, or Firm* — Osha Bergman Watanabe & Burton LLP

(57) ABSTRACT

A rock testing system includes a rock sample having organic matter provided on a stand in a testing device and a photothermal laser that emits a selected wavelength corresponding to an absorption peak of the organic matter. Methods for testing the rock sample include irradiating the rock sample with the photothermal laser to selectively heat the organic matter and monitoring porosity of the rock sample as the organic matter is heated.

19 Claims, 3 Drawing Sheets

(56) References Cited

U.S. PATENT DOCUMENTS

| | | | | |
|---|---|---|---|---|
| 10,948,431 | B1* | 3/2021 | Zheng | G01N 33/24 |
| 2006/0153269 | A1* | 7/2006 | Lakestani | G01N 25/18 |
| | | | | 374/E17.015 |
| 2006/0262903 | A1* | 11/2006 | Diebold | G01N 23/041 |
| | | | | 378/62 |
| 2011/0271738 | A1* | 11/2011 | McGill | G01N 21/64 |
| | | | | 250/338.5 |
| 2015/0068806 | A1* | 3/2015 | Duran Toro | E21B 49/02 |
| | | | | 175/50 |
| 2017/0248532 | A1* | 8/2017 | Kadambi | H01J 35/065 |
| 2018/0335374 | A1* | 11/2018 | Kanj | G01N 33/241 |
| 2019/0120753 | A1* | 4/2019 | Prater | G01N 21/59 |
| 2019/0266719 | A1* | 8/2019 | Kommer | G01N 23/046 |
| 2020/0003694 | A1* | 1/2020 | Sauerer | G01N 21/65 |
| 2020/0182770 | A1* | 6/2020 | Tokonami | B25J 7/00 |
| 2021/0080413 | A1* | 3/2021 | Eichmann | G01N 33/241 |
| 2021/0096090 | A1* | 4/2021 | Maskrot | G01N 33/20 |
| 2022/0146486 | A1* | 5/2022 | Ferreira Da Silva | E21B 43/25 |

FOREIGN PATENT DOCUMENTS

| | | |
|---|---|---|
| CN | 107153032 A | 9/2017 |
| CN | 105300807 B | 2/2018 |
| CN | 107748116 A | 3/2018 |
| CN | 113008671 A | 6/2021 |

OTHER PUBLICATIONS

Vanorio, Tiziana. "Recent advances in time-lapse, laboratory rock physics for the characterization and monitoring of fluid-rock interactions", Geophysics, vol. 80, No. 2. Mar. 2015, pp. 1-11, [11 Pages].

Schepp, Laura L., et al. "Digital rock physics and laboratory considerations on a high-porosity volcanic rock", Scientific Reports. Apr. 3, 2020, pp. 1-16, [16 Pages].

Liu, V. G., et al. "Selective photothermal interaction using an 805-nm diode laser and indocyanine green in gel phantom and chicken breast tissue", Lasers in medical science. Oct. 2002, pp. 1-8, [8 Pages].

* cited by examiner

APPARATUS FOR REAL-TIME MONITORING OF ORGANIC MATTER POROSITY EVOLUTION USING SELECTIVE PHOTO-THERMAL LASER AS A HEAT SOURCE TO TARGET ORGANIC MATTER ONLY

BACKGROUND

Rock characterization is used in formation evaluation in order to provide data representative of a reservoir at in situ conditions and thereby reduce uncertainty in the evaluation of the reservoir. Formation evaluation may be useful for all stages of hydrocarbon recovery, including, for example, developing a well plan and determining production parameters. Different testing apparatuses may be used to test the physical and chemical properties of rock, including downhole testing devices and surface, laboratory testing devices. Different testing apparatuses may provide different data about the rock and have different advantages and disadvantages in terms of accuracy, precision, resolution, and scale.

For example, laboratory testing devices may include pressure and temperature devices that apply pressure and temperature conditions representative of the formation from which the rock sample came. Measurements of different properties of the rock sample may be taken under the simulated pressure and temperature environment to acquire rock characterization data representative of the formation under in situ conditions. Various types of laboratory testing apparatuses may simulate various downhole conditions for acquiring rock characterization data representative of the formation under in situ conditions.

Other types of testing apparatuses may include downhole testing/measuring devices, which may be provided on logging tools and sent downhole to test rock properties downhole. Data collected downhole may be used to evaluate downhole conditions and in situ rock characterizations of a formation.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to testing devices that include a body, a sample stand provided inside the body, a photothermal laser mounted inside the body and spaced apart from the sample stand, and an x-ray source and an x-ray receiver mounted at opposite sides of the body and around the sample stand.

In another aspect, embodiments disclosed herein relate to systems including a testing device having a sample stand, a photothermal laser spaced apart from the sample stand, and a micro-CT scanner. The micro-CT scanner may include an x-ray source and an x-ray receiver, wherein the x-ray source and the x-ray receiver are positioned around opposite sides of the sample stand and are spaced apart from the sample stand. The systems may further include a computing system connected to the micro-CT scanner.

In yet another aspect, embodiments disclosed herein relate to methods where a rock sample having organic matter is provided on a stand in a testing device, and a photothermal laser is provided that emits a selected wavelength corresponding to an absorption peak of the organic matter. Such methods may include irradiating the rock sample with the photothermal laser to selectively heat the organic matter and monitoring porosity of the rock sample as the organic matter is heated.

Other aspects and advantages of the claimed subject matter will be apparent from the following description and the appended claims.

BRIEF DESCRIPTION OF DRAWINGS

Wherever possible, like or identical reference numerals are used in the figures to identify common or the same elements. The figures are not necessarily to scale and certain features and certain views of the figures may be shown exaggerated in scale for purposes of clarification.

DETAILED DESCRIPTION

Embodiments of the present disclosure are described below in detail with reference to the accompanying figures. In the following detailed description, numerous specific details are set forth in order to provide a more thorough understanding of the claimed subject matter. However, it will be apparent to one having ordinary skill in the art that the embodiments described may be practiced without these specific details. In other instances, well-known features have not been described in detail to avoid unnecessarily complicating the description.

Embodiments disclosed herein relate generally to systems and methods for testing porosity evolution in a rock sample using a photothermal laser to target and heat selected material in the rock sample. The photothermal laser may be designed to emit a selected wavelength that corresponds to an absorption peak of the selected material in the rock sample, such that when the photothermal laser irradiates the rock sample, the selected material in the rock absorbs the laser emission and is heated.

By using a photothermal laser to heat selected material in a rock sample, material held in the rock's pores may be targeted and selectively heated without heating the surrounding rock matrix. For example, kerogen is a naturally occurring organic material that may be found in the pores of a source rock. Typical organic constituents of kerogen include algae and woody plant material. Depending on the type of kerogen, kerogen may go through a thermal maturation process that yields oil or gas. As kerogen is heated and goes through thermal maturation, kerogen may change in color (e.g., from yellow-orange to brown to black). According to embodiments of the present disclosure, by using a photothermal laser to selectively heat kerogen within a rock sample, the kerogen may undergo thermal maturation without adversely affecting other materials in the rock sample (e.g., clays), which may allow investigation of porosity evolution in the rock sample as a result of kerogen thermal maturation.

According to embodiments of the present disclosure, a testing device used for monitoring porosity evolution in a rock sample may include a photothermal laser that may selectively heat pore material in the rock sample. The testing device may also include monitoring equipment that may be used to monitor the porosity evolution in the rock sample as the pore material is selectively heated with the photothermal laser.

Figure 1:
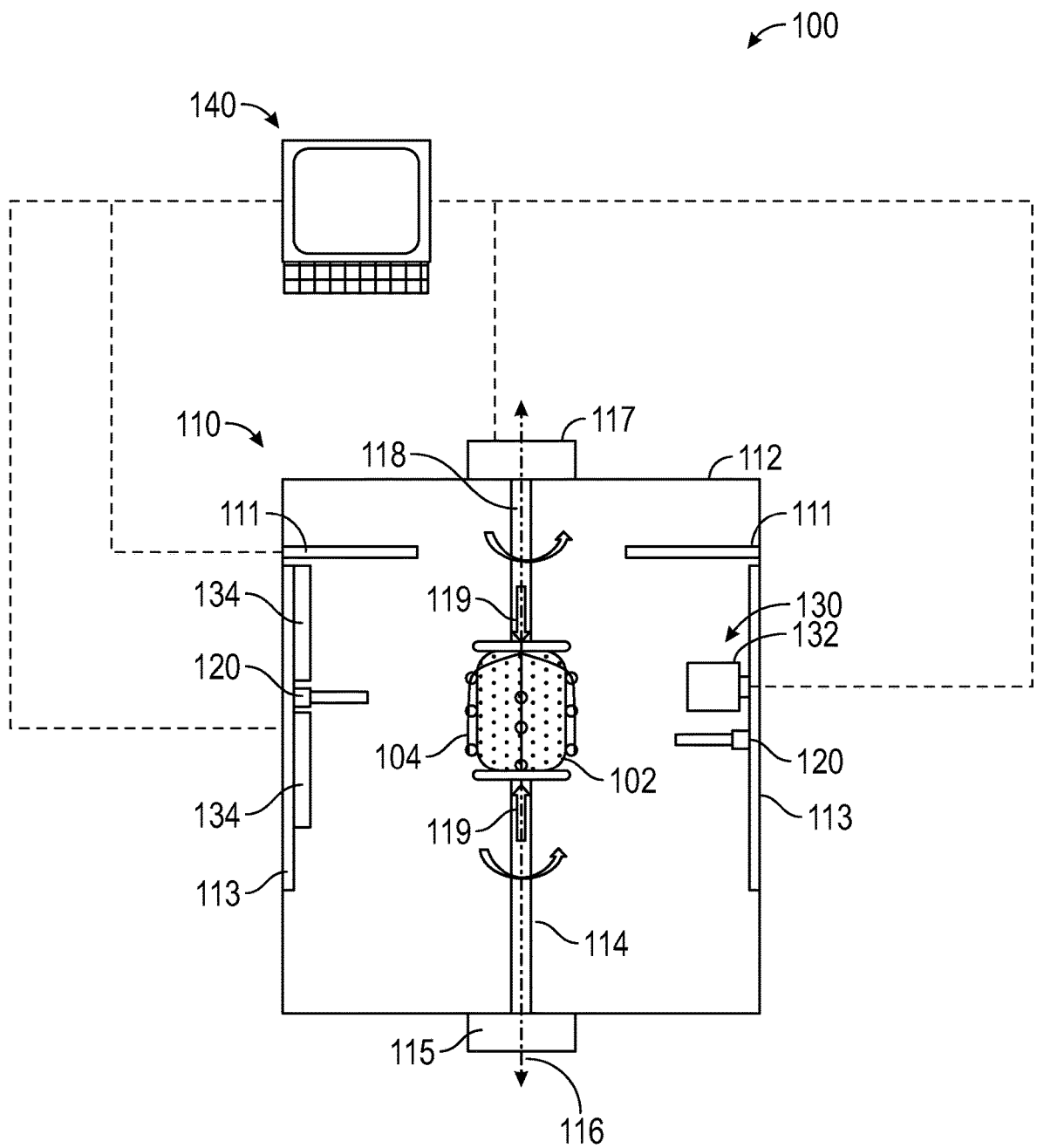
FIG. 1 shows an example of a system according to embodiments of the present disclosure.

For example, FIG. 1 shows an example of a system 100 for testing a rock sample 102 that includes a testing device 110 according to embodiments of the present disclosure. The testing device 110 may include at least one photothermal laser 120 mounted inside a body 112 of the testing device 110 and positioned to be directed toward the rock sample 102.

A photothermal laser 120 may be designed to emit a beam with a selected wavelength that may target and heat a specific material distinguished by color within the rock sample 102. According to embodiments of the present disclosure, a photothermal laser 120 may be a diode laser, where an electrical current may be directed to a diode to create lasing conditions at the diode's junction. Recombination in the diode material may result in emission of radiation with a particular wavelength according to the diode material used. In other words, different diode material may emit radiation having different wavelengths. Thus, a photothermal laser 120 may be designed to emit a selected wavelength by selecting the corresponding diode material to emit the selected wavelength. For example, if a selected material in a rock sample 102 has a black color, which may absorb wavelengths ranging from 400-700 nm, a photothermal laser may be designed to emit a wavelength between 400-700 nm by selecting corresponding diode material to form the photothermal laser. When targeting selected material that has an absorption curve that overlaps with a color of non-selected material in the rock sample, the photothermal laser may be designed to emit a beam with a wavelength that corresponds to an absorption value for the color of the selected material and that does not correspond to an absorption value for the color of the non-selected material.

In some embodiments, more than one photothermal laser 120 may be provided, where each photothermal laser 120 may be designed to emit a different selected wavelength. By providing multiple photothermal lasers 120 with different emission wavelengths, multiple phases of organic material may be targeted for heating. This may allow, for example, for continuous thermal maturation of organic material within a rock sample.

The rock sample 102 may be held on a sample stand 114 provided inside the testing device body 112. The sample stand 114 may include a stage, or platform, on which the rock sample 102 may be held. According to embodiments of the present disclosure, the sample stand 114 may be movable, e.g., using a motor 115. For example, the sample stand 114 may be rotatable about a central axis 116 and/or may be axially movable up and down along the central axis 116.

In some embodiments, a capping stand 118 may also be provided in the body 112, where the capping stand 118 may be co-axially aligned with the sample stand 114 and axially spaced apart from the sample stand 114. The capping stand 118 may be used to hold the rock sample 112 in place on the sample stand 114, where the rock sample 112 may be sandwiched between the sample stand 114 and the capping stand 118. In some embodiments, the capping stand 118 may be rotatable about the central axis 116 (e.g., using a separate motor 117 or the same motor 115 used to rotate the sample stand 114), where the capping stand 118 may rotate in the same direction and at the same speed as the sample stand 114 to rotate a rock sample being held between the two stands. In some embodiments, the capping stand 118 may be axially movable along the central axis 116 (in addition to or alternately to being rotatable), where axial movement of the capping stand 118 may apply a load to the rock sample 112, e.g., for providing uni-axial stress on the rock sample 102 and/or for holding the rock sample 102 in place during testing. In some embodiments, a rock sample 102 may be provided on a sample stand 114 in a testing device without a capping stand 118.

As shown in FIG. 1, the sample stand 114 and the capping stand 118 may extend into the interior of the testing device body 112 to hold a rock sample 102 inside the body 112. In some embodiments, the testing device body 112 may be a framed structure, e.g., having one or more frames that support equipment of the testing device, where the interior of the body 112 may be open to the environment around the testing device. In some embodiments, the testing device body 112 may be an enclosed structure, e.g., having walls that are capable of fully enclosing the interior of the body 112. When a testing device body 112 is an enclosed structure, the body 112 may include one or more removable walls that act as a lid (which may open and close to allow access inside the body 112) or may include one or more other type of sealable port that may open and close to allow access inside the body 112.

According to embodiments of the present disclosure, a photothermal laser 120 may be mounted directly, or indirectly, to a wall or a frame of the body 112. In some embodiments, the photothermal laser 120 may be mounted on tracks 113 in the body 112, where the photothermal laser 120 may be moved to different positions in the body 112 along the tracks 113. The tracks 113 may extend axially along the testing device 110 (such that the photothermal laser 120 may be axially moved along the body 112) and/or may extend circumferentially around the testing device 110 (such that the photothermal laser 120 may be moved circumferentially along the body 112). In some embodiments, a photothermal laser 120 may be manually moved to different locations in the body 112. In some embodiments, the photothermal laser 120 may be fixed in a single location along the testing device body 112.

According to embodiments of the present disclosure, at least one of the sample stand 114 and the photothermal laser 120 may be axially movable within the body 112, such that the sample stand 114 and the photothermal laser 120 are axially movable with respect to each other. Additionally, or alternatively, the sample stand 114 may be rotationally movable and/or the photothermal laser 120 may be circumferentially movable around the body 112, such that the sample stand 114 and the photothermal laser 120 are rotationally movable with respect to each other.

By providing at least one of a movable sample stand 114 and a movable photothermal laser 120, the rock sample 102 and the photothermal laser 120 may be movable with respect to each other during testing, which may allow the photothermal laser 120 to radiate multiple portions of the rock sample 102. For example, the photothermal laser 120 and rock sample 102 may be axially moved with respect to each other to allow the photothermal laser 120 to radiate the entire axial length of the rock sample 102. According to embodiments of the present disclosure, relative movement between the rock sample 102 and the photothermal laser 120 may be used to direct a beam from the photothermal laser 120 to contact the entire (or almost all of the) rock sample 102. In such manner, the entire amount of the selected material in the rock sample 102 may be uniformly heated by the photothermal laser 120. For example, in some embodiments, the rock sample 102 may be rotated and the photothermal laser 120 may be moved axially while the photothermal laser 120 directs a beam toward the rock sample 102 in order to uniformly heat selected material in all parts of the rock sample 102. In some embodiments, the rock sample 102 may be rotated and moved axially while the photothermal laser 120 directs a beam toward the rock sample 102 from a stationary position in order to uniformly heat selected material in all parts of the rock sample 102.

As selected material in the rock sample 102 is heated with the photothermal laser 120, pressure may be applied to the rock sample 102. In some embodiments, a pressure representative of a downhole pressure may be applied to simulate downhole conditions in a formation represented by the rock sample 102. For example, a pressure of up to about 20,000 psi may be applied to the rock sample 102 while it is being irradiated with the photothermal laser 120.

According to embodiments of the present disclosure, pressure may be applied to the rock sample 102 using a pressure unit provided with the testing device 110. The type of pressure unit used may be selected based on the type of pressure applied to the rock sample 102. For example, in the embodiment shown in FIG. 1, the pressure unit may be formed by the combination of the sample stand 114 and the capping stand 118, where at least one of the sample stand 114 and the capping stand 118 is axially movable to apply uniaxial stress (represented by arrows 119) to a rock sample 102 sandwiched between the sample stand 114 and the capping stand 118.

Figure 2:
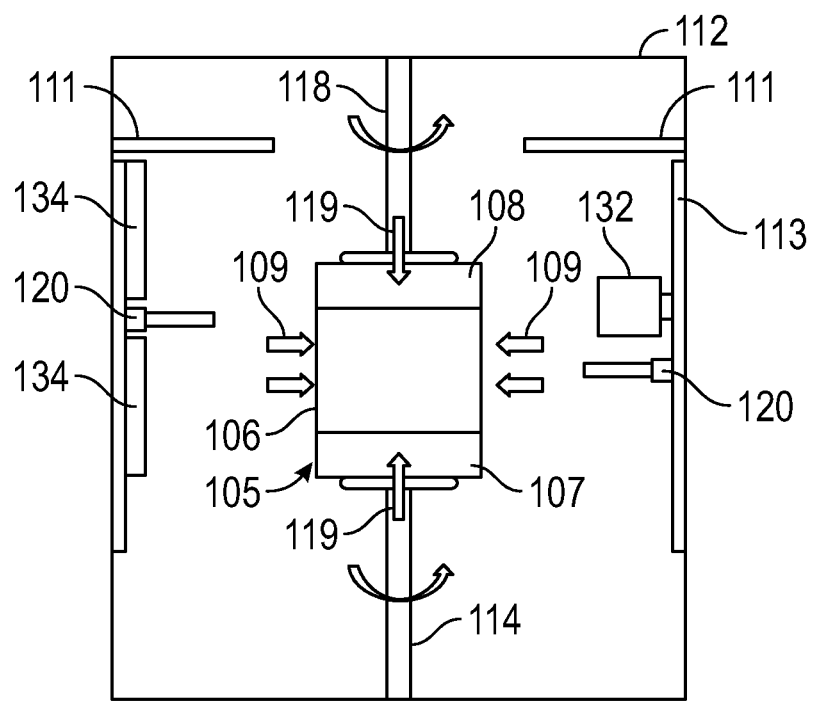
FIG. 2 shows an example of a testing device according to embodiments of the present disclosure.

In other embodiments, a pressure unit may include a pressure vessel and/or a pressure pump to generate triaxial stress on the rock sample. For example, FIG. 2 shows an alternative embodiment of the testing device 110 including a pressure unit, where the pressure unit includes a pressure vessel 105 for applying triaxial stress on a rock sample. The pressure vessel 105 may include a sleeve 106, a base 107 positioned at a lower end of the sleeve 106, and a cap 108 positioned at an opposite, upper end of the sleeve 106. A rock sample may be confined inside the pressure vessel 105 between the base 107 and cap 108. Axial stress (represented by arrows 119) may be applied in the axial direction, e.g., using a piston, and confining pressure (represented by arrows 109) may be applied in the radial direction, e.g., using confining fluid, to a rock sample confined in the pressure vessel to provide triaxial stress pressure on the rock sample. The pressure vessel sleeve 106 may be made of a material that allows a photothermal laser and an imaging device to transmit through the sleeve.

In some embodiments, a pressure vessel may be selected from various types of high pressure, high temperature (HPHT) reactors for inducing different processes in a rock sample (e.g., in situ pyrolysis of organic matter in shale, decarbonation of limestone, and alkali-driven geopolymerization of aluminosilicates). As a first example, a reactor system may include an internally-heated pressure vessel with a maximum pressure rating of 34.5 MPa at 510° C. The reactor system may be a 1 L volume bolted closure autoclave heated by a 200 W ceramic refractory heater. Samples may be jacketed by annealed copper tubing to separate the pore fluid and confining pressures and thermally isolated by cylindrical alumina spacers on either end. As second example, a reactor system may include a standard pressure vessel (e.g., general purpose vessels sold by PARR Instrument Company such as their Series 4760 General Purpose Pressure Vessel) with an external heater selected for small batch reactions (including caustic solutions) at pressures and temperatures up to 20 MPa and 350° C., respectively.

According to embodiments of the present disclosure, various types of standard pressure vessels known to be used for rock measurements may be used in conjunction with testing devices (e.g., including a photothermal laser and scanner system) described herein. In some embodiments, standard pressure vessels may be used in conjunction with testing devices described herein without modifying the standard pressure vessel.

As selected material in the rock sample 102 is heated with the photothermal laser 120, porosity evolution within the rock sample 102 may be monitored using one or more monitoring devices in the testing device 110. For example, according to embodiments of the present disclosure, a testing device 110 may include one or more different types of sensors which may be used to monitor properties indicating porosity evolution in the rock sample 102 as it is targeted by the photothermal laser 120.

In some embodiments, one or more sensors may be attached to the rock sample 102 to monitor characteristics of the rock sample 102 as it undergoes testing. For example, as shown in FIG. 1, velocity and strain sensors 104 may be attached to the rock sample 102 to measure changing forces and deformation of the rock sample 102 during testing. Such measurements may be used to determine the effects of changing porosity in the rock sample 102 on the elastic properties of the rock as porous material is heated by the photothermal laser.

In some embodiments, one or more chemical sensors 111 may be provided in the testing device 110 to measure a chemical composition in the testing device 110. For example, a chemical sensor 111 may be mounted on a wall or other support structure in the testing device 110. In some embodiments, chemical sensors 111 may be used in combination with enclosed testing devices, where one or more chemical sensors 111 may be enclosed inside a testing device body 112. Enclosing a chemical sensor 111 within a testing device 110 during testing of the rock sample 102 may improve detection of chemicals generated during the testing.

Different types of chemical sensors 111 may be used to detect different chemicals. For example, in embodiments where a kerogen pore material (e.g., type III kerogen material) is targeted and heated by the photothermal laser 120, the kerogen may generate a hydrocarbon gas. When the hydrocarbon gas escapes the rock sample 102, a chemical sensor 111 capable of detecting hydrocarbon gas may detect changing amounts of the hydrocarbon gas in the testing device environment released from the rock sample 102. In such manner, the chemical sensor 111 may indicate gas formation from the rock sample 102, which may be used in analysis of the porosity evolution in the rock sample 102 as it is targeted by the photothermal laser 120.

Additionally, according to embodiments of the present disclosure, porosity evolution within the rock sample 102 may be monitored using one or more imaging devices. For example, according to embodiments of the present disclosure, a testing device 110 may include an imaging device, such as a computed tomographic (CT) imaging device (e.g., a conventional CT scanner, a micro-CT scanner, nano-CT scanner, or synchrotron CT scanner) to visualize rock-pore systems in a rock sample 102. A CT scanner may be used to take measurements (e.g., x-ray measurements) around the rock sample 102 to produce different cross-sectional images corresponding to different slices of the rock sample 102. The cross-sectional images may be layered together and processed to generate 3-dimensional (3D) volumes between the layers and form a digital model of the rock sample, which can reveal the internal features of the rock sample 102. In some embodiments, for example, a micro-CT scan may provide a non-destructive technique for 3D imaging of the pore space in the rock sample 102 at a resolution of several microns.

For example, as shown in FIGS. 1 and 2, a testing device 110 may include a micro-CT scanner 130 having an x-ray source 132 and at least one x-ray receiver 134. The x-ray source 132 and x-ray receiver(s) 134 may be arranged around the testing device 110 in a position to take images of a rock sample 102 held on the sample stand 114 as selected material in the rock sample 102 is heated with the photothermal laser 120. For example, an x-ray source 132 and an x-ray receiver 134 may be spaced apart from and positioned around opposite sides of the sample stand 114 and rock sample 102. X-rays from the x-ray source 132 may be transmitted through the rock sample 102 and recorded by the x-ray receiver(s) as a 2-dimensional (2D) image (a CT scan). CT scans may be taken by the micro-CT scanner 130 as the x-ray source 132 rotates around the rock sample 102, or as the rock sample 102 rotates within the source beam. For example, the x-ray source 132 and the x-ray receiver 134 may be rotatable around the sample stand, e.g., via a track system around a perimeter of the testing device body 112. In such embodiments, the body 112 of the testing device may have a circumferential perimeter around which the micro-CT scanner 130 may be moved. By taking CT scans as the rock sample 102 and micro-CT scanner 130 are rotated relative to each other, a series of CT scans may be taken of part of or the entire rock sample 102. Serial CT scans from the micro-CT scanner 130 may then be compiled together to construct a 3D digital model of the rock sample 102.

Resolution of the generated 3D digital model may be, for example, on the millimeter to micron to sub-micron scale, depending on the CT device used. Petrophysical calculations, such as porosity and permeability, depend on, for example, the segmentation of pixels into rock vs. pore. Segmentation may be difficult if some of the pores are smaller than the resolution of the micro-CT scanner 130. Bulk density of the rock sample 102 may be computed from x-ray attenuation coefficients, which is a characteristic of the rock material used to identify one or more rock material segments in the rock sample, and thus help in identifying the pore structure of the rock sample 102.

Figure 3:
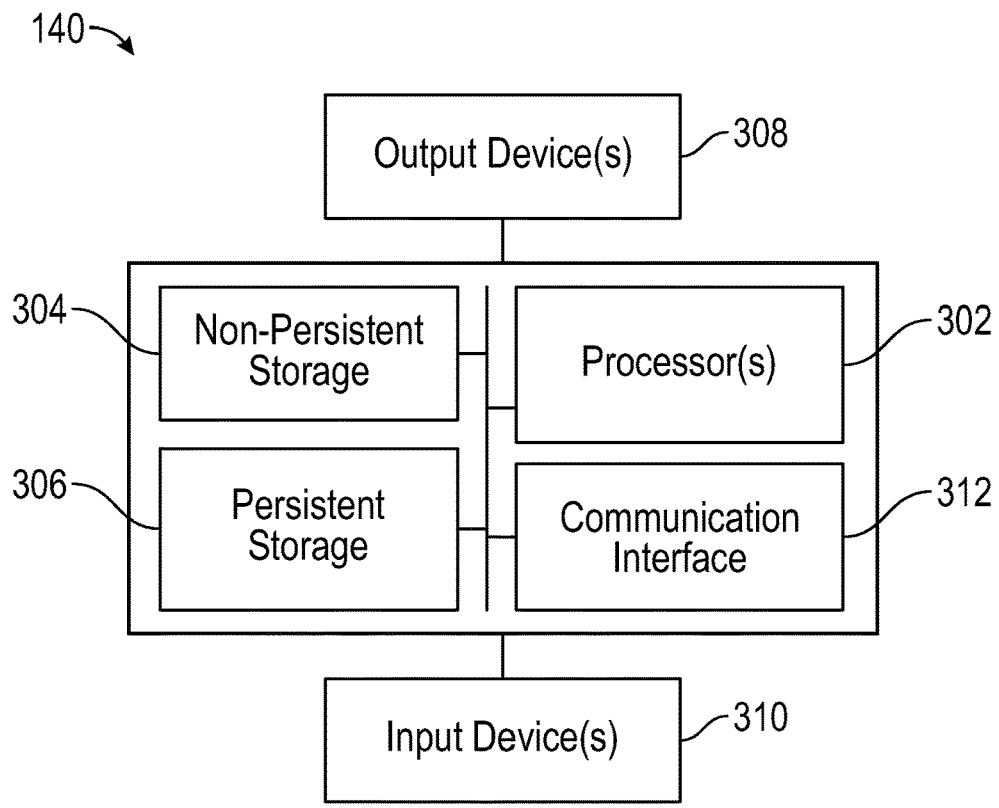
FIG. 3 shows an example of a computing system that may be used with systems and methods according to embodiments of the present disclosure.

Images taken by the imaging device may be sent to a computing system 140 for processing, as shown in FIG. 1. Any combination of mobile, desktop, server, router, switch, embedded device, or other types of hardware may be used for the computing system 140. For example, as shown in FIG. 3, the computing system 140 may include one or more computer processors 302, non-persistent storage 304 (e.g., volatile memory, such as random access memory (RAM), cache memory), persistent storage 306 (e.g., a hard disk, an optical drive such as a compact disk (CD) drive or digital versatile disk (DVD) drive, a flash memory, etc.), a communication interface 312 (e.g., Bluetooth interface, infrared interface, network interface, optical interface, etc.), and numerous other elements and functionalities.

The computer processor(s) 302 may be an integrated circuit for processing instructions. For example, the computer processor(s) may be one or more cores or micro-cores of a processor. The computing system 140 may also include one or more input devices 310, such as a touchscreen, keyboard, mouse, microphone, touchpad, electronic pen, or any other type of input device.

The communication interface 312 may include an integrated circuit for connecting the computing system 140 to a network (not shown) (e.g., a local area network (LAN), a wide area network (WAN) such as the Internet, mobile network, or any other type of network) and/or to another device, such as another computing device.

Further, the computing system 140 may include one or more output devices 308, such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) 302, non-persistent storage 304, and persistent storage 306. Many different types of computing systems exist, and the aforementioned input and output device(s) may take other forms.

Referring again to FIG. 1, a computing system 140 may be connected to one or more components of a testing device 110, including, for example, testing components used to perform testing/apply testing parameters to a rock sample 102 and detecting components used to detect or sense resulting parameters from the testing.

For example, the computing system 140 may be connected to testing components, such as the photothermal laser 120, a pressure unit, and/or a stand 114, 118. The computing system 140 may be connected to a controller of a testing component in order to control the testing component using the computing system 140. For example, the computing system 140 may send instructions to a controller of the photothermal laser 120 to operate the photothermal laser 120, including, for example, to control the position/orientation of the photothermal laser 120 and to control the frequency and duration of emitting a beam from the photothermal laser 120. In some embodiments, the computing system 140 may be connected to a controller of a pressure unit to operate the pressure unit, including, for example, to control the amount of pressure applied to a rock sample and timing for when pressure is applied. For example, the computing system 140 may send instructions to a pressure unit controller to correspond operation of the pressure unit with the photothermal laser to apply pressure to a rock sample while being heated with the laser. In some embodiments, the computing system 140 may be connected to an operating component (e.g., a controller or motor) of a stand to operate the stand, including, for example, to rotate or axially move the stand (e.g., sample stand 114 and/or capping stand 118).

By using a computing system 140 to operate testing components in a testing device 110, testing may be done automatically and according to a preset program. For example, the computing system 140 may send instructions to the testing device 110 to concurrently apply a preselected pressure to a rock sample, emit a beam from a photothermal laser 120 on the rock sample, and move the rock sample (via rotational and/or axial movement of a stand holding the rock sample).

Additionally, the computing system 140 may be connected to one or more detecting components of the testing device 110, such as sensors (e.g., chemical sensors 111 and/or velocity and strain sensors 104), the micro-CT scanner 130, and/or other imaging device provided in the testing device 110. Data collected from one or more of the detecting components of a testing device 110 may be sent to the computing system 140 for processing. In some embodiments, the computing system 140 may send instructions for operation of a detecting component. For example, the computing system 140 may send instructions to a controller of the micro-CT scanner 130 to operate the micro-CT scanner 130, including, for example, to control the position of the micro-CT scanner 130 relative to a rock sample held in the testing device 110 and timing for taking images of the rock sample as the micro-CT scanner 130 and rock sample are moved relative to each other.

In some embodiments, data collected from a detecting component may be used to make a decision in controlling a component in the testing device 110. For example, when an image is taken by a micro-CT scanner 130, the computing system 140 may send instructions to the micro-CT scanner 130 or a stand (e.g., sample stand 114 and capping stand 118) to rotate before taking another image. In some embodiments, the computing system 140 may send instructions to the testing device 110 to reduce pressure applied to a rock sample 102 after receiving data from velocity and strain sensors 104 on a rock sample indicating a failure in the rock sample 102.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure. For example, the computing system 140 may include software programs to perform methods disclosed herein, including processing images taken of a rock sample 102 in a testing device 110 and generating a 3D digital model of the rock sample 102 from images taken of the rock sample 102.

Figure 4:
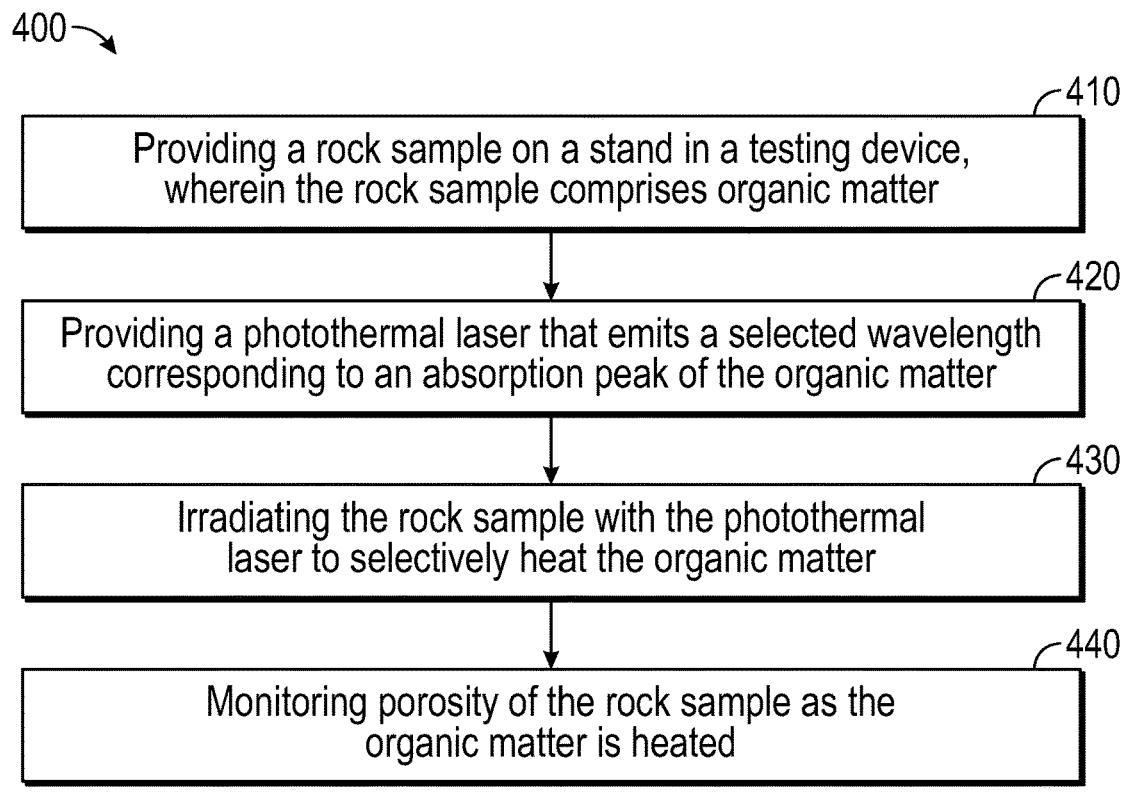
FIG. 4 shows a method according to embodiments of the present disclosure.

Referring now to FIG. 4, FIG. 4 shows an example of a method 400 according to embodiments of the present disclosure. One or more steps shown may be omitted or repeated. According to embodiments of the present disclosure, a computing system (e.g., 140 in FIG. 1) may be used to perform one or more steps of the method 400 using a testing device (e.g., 110 in FIG. 1 or FIG. 2).

As shown, the method 400 may include providing a rock sample on a stand in a testing device (step 410). The rock sample may be a rock representative of a downhole formation, where the rock sample may include organic matter contained within pores of the rock. For example, the rock sample may be a shaley rock containing clay, cement, fluids, and organic matter (e.g., kerogen or other hydrocarbon material).

A photothermal laser may be provided in the testing device and oriented to emit a beam to the rock sample (step 420). The photothermal laser may be designed to emit a beam with a selected wavelength that corresponds to an absorption peak of organic matter in the rock sample, such as kerogen.

The photothermal laser may irradiate the rock sample with the beam to selectively heat the organic matter within the rock sample (step 430). In some embodiments, the rock sample may be rotated and/or moved axially as the rock sample is irradiated by the photothermal laser, such that the photothermal laser may irradiate all or most of the organic matter within the rock sample. By irradiating the rock sample with a beam having a wavelength that corresponds with an absorption peak of a selected material in the rock sample (e.g., a selected organic material), the selected material may be heated by the beam without heating other rock material (e.g., clays). For example, selective heating from a photothermal laser may target the darkest components in a rock sample such as kerogen to stimulate thermal evolution and hydrocarbon production without destroying clays or evaporating bounding water in the rock sample.

According to embodiments of the present disclosure, pressure may be applied to the rock sample while the rock sample is selectively heated by the photothermal laser. For example, a pressure that is within a range of a downhole pressure may be applied to the rock sample in order to simulate a downhole condition. Pressure may be applied to the rock sample using a pressure unit provided with the testing device.

The porosity of the rock sample may be monitored as the selected material (e.g., selected organic matter) is heated (step 440). For example, chemical sensors may be provided in the testing device to sense chemical changes in the testing device as the selected material is heated. In some embodiments, changes in elastic properties of the rock sample may be measured as the selected material is heated using velocity and strain sensors positioned around the rock sample in the testing device.

According to embodiments of the present disclosure, monitoring the porosity of the rock sample as the selected material is heated may include taking images of the rock sample, for example, taking x-rays of the rock sample using a CT scanner. Image data may be used to generate a 3D digital model of the rock sample showing the porosity of the rock sample.

In contrast to rock testing devices conventionally used to characterize rock under elevated temperatures representative of downhole conditions, devices and systems according to embodiments may use a photothermal laser to selectively heat small portions of a rock sample rather than the entire rock sample. Using testing devices according to embodiments of the present disclosure, a photothermal laser may heat selected material within a rock sample without damaging other, non-selected material in the rock sample. Such devices and methods may be useful, for example, when testing clay-rich source rocks, where pyrolysis may be performed on the kerogen (from heating via a photothermal laser) without heating up the clay or damaging the water bounds they carry. Testing devices disclosed herein may also be equipped with sensors to detect any chemical changes and elastic properties in real-time, e.g., using chemical sensors, velocity, and strain sensors. Additionally, a CT scanner may be used to monitor the porosity evolution as a result of the increase in temperature from the photothermal laser, including, for example, porosity evolution from heating kerogen beyond the oil and gas windows.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. An apparatus, comprising:
    a body;
    a sample stand provided inside the body;
    a photothermal laser mounted inside the body and spaced apart from the sample stand; and
    an x-ray source and an x-ray receiver mounted at opposite sides of the body and around the sample stand;
    wherein the x-ray source and the x-ray receiver are rotatable around the sample stand.

2. The apparatus of claim 1, further comprising a capping stand provided in the body, wherein the capping stand is co-axially aligned with the sample stand and axially spaced apart from the sample stand.

3. The apparatus of claim 1, further comprising a pressure vessel provided on the sample stand.

4. The apparatus of claim 1, wherein the sample stand is rotatable about a central axis.

5. The apparatus of claim 1, further comprising chemical sensors provided in the body.

6. The apparatus of claim 1, wherein the sample stand and the photothermal laser are axially movable with respect to each other.

7. A system, comprising:
a testing device comprising:
- a sample stand;
- a photothermal laser spaced apart from the sample stand; and
- a micro-CT scanner comprising:
  - an x-ray source; and
  - an x-ray receiver;
  wherein the x-ray source and the x-ray receiver are positioned around opposite sides of the sample stand and are spaced apart from the sample stand; and
a computing system connected to the micro-CT scanner.

8. The system of claim 7, wherein the sample stand and at least one of the micro-CT scanner and the photothermal laser are axially movable with respect to each other.

9. The system of claim 7, further comprising a pressure unit provided in the testing device.

10. The system of claim 7, further comprising a chemical sensor in the testing device, wherein the computing system is also connected to the chemical sensor.

11. The system of claim 7, further comprising a rock sample having organic matter contained within pores of the rock sample, wherein the photothermal laser is configured to emit a selected wavelength corresponding to an absorption peak of the organic matter.

12. A method, comprising:
providing a rock sample on a stand in a testing device, wherein the rock sample comprises organic matter;
providing a photothermal laser that emits a selected wavelength corresponding to an absorption peak of the organic matter;
irradiating the rock sample with the photothermal laser to selectively heat the organic matter; and
monitoring porosity of the rock sample as the organic matter is heated.

13. The method of claim 12, wherein monitoring the porosity comprises taking x-ray images of the rock sample.

14. The method of claim 12, further comprising rotating the stage stand to rotate the rock sample while the rock sample is irradiated by the photothermal laser.

15. The method of claim 12, further comprising applying pressure to the rock sample.

16. The method of claim 12, further comprising sensing chemical changes in the testing device as the organic matter is heated.

17. The method of claim 12, wherein the organic matter is kerogen.

18. The method of claim 12, further comprising measuring changes in elastic properties of the rock sample using velocity and strain sensors positioned around the rock sample.

19. The method of claim 13, wherein the monitoring of the porosity further comprises compiling image data from the x-ray images to generate a 3D model of the rock sample showing the porosity of the rock sample.

* * * * *